(12) United States Patent
Ogawa et al.

(10) Patent No.: US 8,049,896 B2
(45) Date of Patent: Nov. 1, 2011

(54) DETECTING ELEMENT, DETECTING DEVICE, AND METHOD OF PRODUCING THE DETECTING ELEMENT

(75) Inventors: Miki Ogawa, Machida (JP); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 737 days.

(21) Appl. No.: 12/125,543

(22) Filed: May 22, 2008

(65) Prior Publication Data
US 2008/0297802 A1 Dec. 4, 2008

(30) Foreign Application Priority Data
May 31, 2007 (JP) ................................. 2007-145287

(51) Int. Cl.
*G01N 21/55* (2006.01)
(52) U.S. Cl. ........................................................ 356/445
(58) Field of Classification Search .................... None
See application file for complete search history.

(56) References Cited

U.S. PATENT DOCUMENTS

| | | | |
|---|---|---|---|
| 7,079,250 B2 | 7/2006 | Mukai | |
| 7,501,649 B2 * | 3/2009 | Naya et al. | 257/9 |
| 2003/0173501 A1 * | 9/2003 | Thio et al. | 250/216 |
| 2004/0183176 A1 | 9/2004 | Naya et al. | |
| 2007/0090411 A1 | 4/2007 | Naya et al. | |
| 2008/0073509 A1 | 3/2008 | Ban et al. | 250/288 |
| 2009/0153866 A1 * | 6/2009 | Yamamichi et al. | 356/445 |

FOREIGN PATENT DOCUMENTS

| | | |
|---|---|---|
| JP | 2003-268592 | 9/2003 |
| JP | 2004-279364 | 10/2004 |

OTHER PUBLICATIONS

J. Aizpurua et al., "Optical Properties of Gold Nanorings", Physical Review Letters, Feb. 7, 2003, pp. 057401-1 to 057401-4, vol. 90, No. 5.

* cited by examiner

*Primary Examiner* — Michael A Lyons
*Assistant Examiner* — Amanda Merlino
(74) *Attorney, Agent, or Firm* — Fitzpatrick, Cella, Harper & Scinto

(57) ABSTRACT

A detecting element for detecting a target substance in a sample includes a substrate having a pore, in which a thickness direction of the substrate corresponds to a depth direction of the pore, and plurality of metal structures disposed in the pore. The plurality of metal structures have a ring shape.

13 Claims, 9 Drawing Sheets

DETECTING ELEMENT, DETECTING DEVICE, AND METHOD OF PRODUCING THE DETECTING ELEMENT

BACKGROUND OF THE INVENTION

1. Field of the Invention

The present invention relates to a detecting element to which plasmon resonance is applied, a detecting device, and a method of producing the detecting element.

2. Description of the Related Art

In recent years, a sensor utilizing localized plasmon resonance using metal fine particles has been attracting attention.

For example, Japanese Patent Application Laid-Open No. 2003-268592 discloses an invention in which mutually isolated metal particles are formed in a plurality of pores in anodized alumina to form a plasmon resonance device. In the device, by utilizing the pores in the anodized alumina, the metal particles can be regularly placed independently with an arbitrary uniform size in arbitrary arrangement, to thereby improve and stabilize sensor sensitivity.

Japanese Patent Application Laid-Open No. 2004-279364 discloses a sensor chip with the aim of providing a sensor having low optical noise and high sensitivity. The sensor chip includes a holding member having a plurality of micropores independent of each other along a direction substantially perpendicular to the surface, and metal fine particles held independently of each other in the plurality of micropores, and is characterized in that the holding member is formed from a transparent dielectric with uniform density.

However, in the inventions disclosed in Japanese Patent Application Laid-Open Nos. 2003-268592 and 2004-279364, the number of the metal fine particles held in one pore is actually one, and thus there has been a limit of the amount of gold particles held on a chip. Therefore, there has been a limit of the number of gold particles per unit area. Moreover, when it is attempted to form a plurality of metal fine particles in one pore, the metal fine particles come into contact with each other. Thus, the dimension and shape of the metal fine particles are likely to become nonuniform. In order to improve and stabilize sensor sensitivity as a plasmon resonance device, it is important that metal fine particles isolated from each other are provided in uniform size.

Moreover, the patent documents disclosing the above prior art technologies do not describe the shape of metal fine particles in detail. More specifically, the above-mentioned patent documents neither describe nor suggest the point of achieving an improvement in sensitivity by controlling the shape of gold particles.

SUMMARY OF THE INVENTION

The present invention can provide a detecting element with high sensitivity, a detecting device, and a method of producing the detecting element.

An aspect of the present invention provides a detecting element for detecting a target substance in a sample including: a substrate; and a metal structure, in which: the substrate has a pore in which the thickness direction of the substrate corresponds to the depth direction of the pore and in which part of the substrate forming the pore constitutes part of the outer surface of the substrate; the metal structure exists in the pore; and the metal structure has a ring shape.

The pore preferably penetrates through the substrate.

The pore preferably includes a plurality of columnar parts in which the depth direction of the pore corresponds to the height direction of the plurality of columnar parts and a part for connecting the plurality of columnar parts, and the metal structure preferably exists in the part for connecting the plurality of columnar parts.

A pore diameter of a pore which appears in a cross section cut along a first plane perpendicular to the thickness direction of the substrate and a pore diameter of a pore which appears in a cross section cut along a second plane perpendicular to the thickness direction of the substrate are preferably different from each other.

The metal structure preferably includes gold or silver.

The number of the metal structures included in one pore is preferably two or more.

The metal structure preferably has, on the surface thereof, a capturing component for capturing the target substance in the sample.

Another aspect of the present invention provides a device for detecting a target substance in a sample by utilizing a plasmon resonance method, the device including: the detecting element; a holding mechanism for holding the detecting element; a light source for irradiating the detecting element with light; and a light receiving element for detecting light emitted from the detecting element.

The detecting device preferably further includes a reaction chamber for bringing the sample into contact with the detecting element.

Still another aspect of the present invention provides a method of producing a detecting element for detecting a target substance in a sample by utilizing a plasmon resonance method of producing a detecting element including: preparing a substrate having a pore in which the thickness direction of the substrate corresponds to the depth direction of the pore and in which part of the substrate forming the pore constitutes part of the outer surface of the substrate; and producing a ring-shaped metal structure in the pore by projecting a material for forming the metal structure in a direction crossing the depth direction of the pore.

The pore preferably includes a plurality of columnar parts in which the depth direction of the pore corresponds to the height direction of the plurality of columnar parts and a part for connecting the plurality of columnar parts.

Still another aspect of the present invention provides a detecting element for detecting a target substance in a sample by utilizing a plasmon resonance method, the detecting element including: a substrate having a contact surface with the sample; a pore having an opening on the contact surface and oriented in the thickness direction of the substrate; and a metal structure provided in the pore, in which the metal structure has a ring shape.

Still another aspect of the present invention provides a detecting device for detecting a target substance in a sample by utilizing a plasmon resonance method, the detecting device including: a holding mechanism for holding the detecting element structured as above; a light source for irradiating the detecting element with light; and a light receiving element for detecting characteristics of light reflected from or transmitted through the detecting element.

Still another aspect of the present invention provides a method of producing a detecting element for detecting a target substance in a sample utilizing a plasmon resonance method, the method including: preparing a substrate which has a pore having an opening on a contact surface with the sample and oriented in the thickness direction of the substrate; and producing a metal structure having a ring shape in the pore by projecting a material for forming the metal structure from an oblique direction with respect to the opening direction of the pore.

Further features of the present invention will become apparent from the following description of exemplary embodiments with reference to the attached drawings.

BRIEF DESCRIPTION OF THE DRAWINGS

FIGS. 5A, 5B, 5C and 5D are conceptual diagrams each illustrating an oblique film deposition method.

DESCRIPTION OF THE EMBODIMENTS

Next, an example of an embodiment of the present invention will be described in detail. First, a detecting element according to the present invention will be described.

The detecting element of the present invention has a structure for detecting a target substance in a sample by utilizing a plasmon resonance method. Basically, the detecting element of the present invention at least includes a substrate and a metal structure provided in each of micropores of the substrate. The substrate has a contact surface with a sample. The micropores open on the contact surface, and are formed so that their depth directions corresponds to the thickness direction of the substrate from the contact surface. The metal structure provided in the micropore has a ring shape.

In other words, the detecting element of the present invention is a detecting element for detecting a target substance in a sample, the detecting element including a substrate and a metal structure, in which the substrate has a pore in which the thickness direction of the substrate corresponds to the depth direction of the pore and in which part of the substrate forming the pore constitutes part of the outer surface of the substrate, the metal structure exists in the pore, and the metal structure has a ring shape.

Figure 1A:
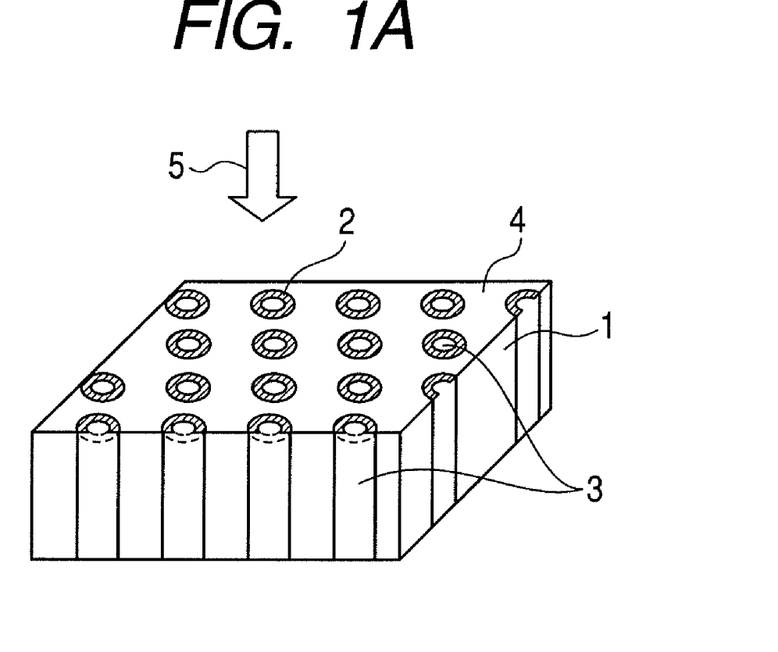
FIGS. 1A and 1B are schematic views each illustrating an example of a detecting element including a substrate and a metal structure according to the present invention.
Figure 1B:
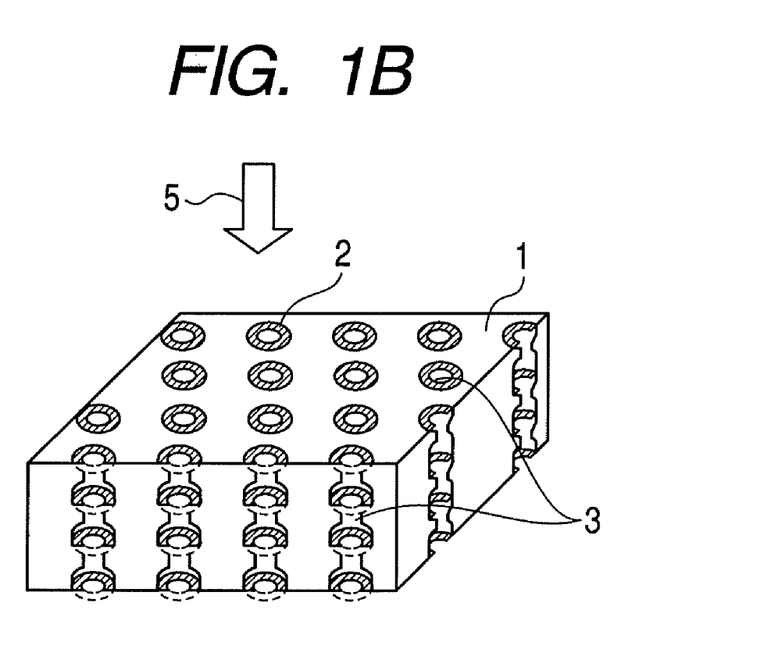

An example of the detecting element according to the present invention is illustrated in FIGS. 1A and 1B.

FIG. 1A is a view illustrating an example in which one metal structure is provided in one pore, and FIG. 1B illustrates an example in which a plurality of metal structures are provided in one pore.

FIG. 1A includes a substrate 1, a metal structure 2, and a pore 3 which belongs to the substrate 1.

Hereinafter, each unit will be described.

(Substrate)

The substrate 1 is used which has a pore 3 (in other words, a micropore), and has material and a shape required for detecting a target substance by utilizing plasmon resonance of the metal structure 2 having a ring shape which exists in the pore 3. Therefore, the substrate 1 is usually formed of a material different from a material for forming the metal structure. Further, the substrate is formed from a material in which the pore for holding the ring-shaped metal structure can be formed as illustrated in FIG. 1. Therefore, there is no limitation on the material and the shape of the substrate insofar as the pore capable of holding the metal structure can be formed on the substrate and the material has resistance to a sample liquid. It is possible to use any materials such as inorganic materials (e.g., glass), organic materials (e.g., resin), semiconductor materials (e.g., silicon), and metal materials different from a material forming the metal structure.

The pore 3 is one in which the thickness direction of the substrate 1 corresponds to the depth direction of the pore and in which part of the substrate forming the pore constitutes part of the outer surface of the substrate. In other words, a face forming the end portion of the pore 3 is a contact surface 4 with a sample 5. Herein, that "A constitutes part of the outer surface of B" means that A constitutes part of the contact portion between B and the outside air. For example, when a liquid is attached to B from the outside, the liquid is attached to A. It is preferable that the central axis of the pore in the thickness direction of the substrate is perpendicular to the surface forming the end portion of the pore 3. Here, in the present invention, that "A and B are perpendicular to each other" means that the angle between A and B is 85° or more and 95° or less, and preferably 87° or more and not more than 93° or less.

Figure 2A:
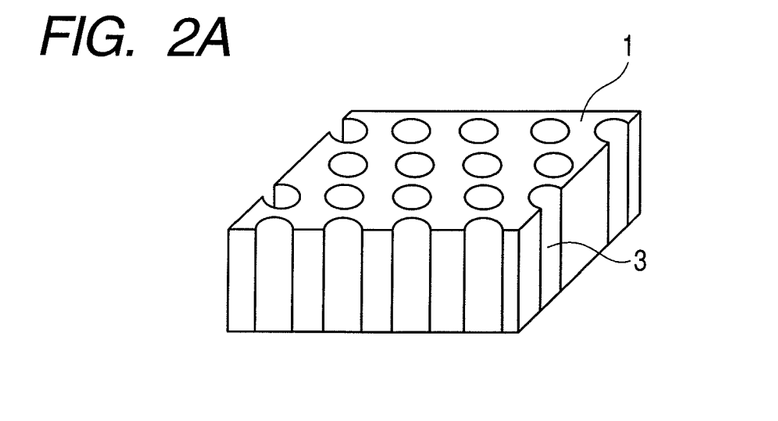
FIGS. 2A, 2B and 2C are schematic views each illustrating an example of the detecting element including a substrate and a metal structure according to the present invention.
Figure 2B:
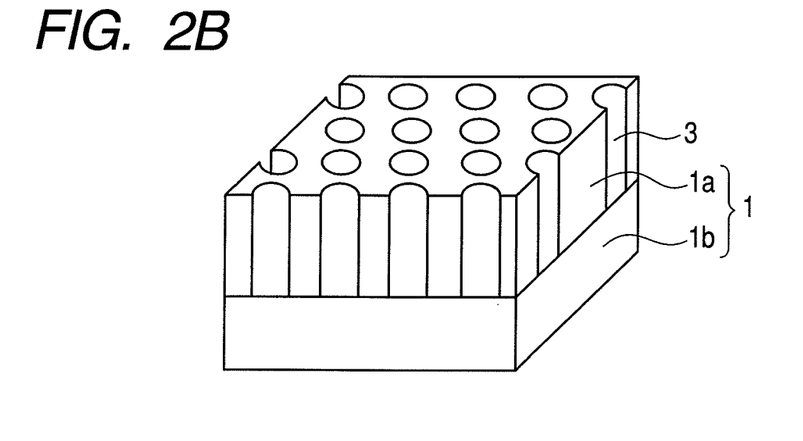
Figure 2C:
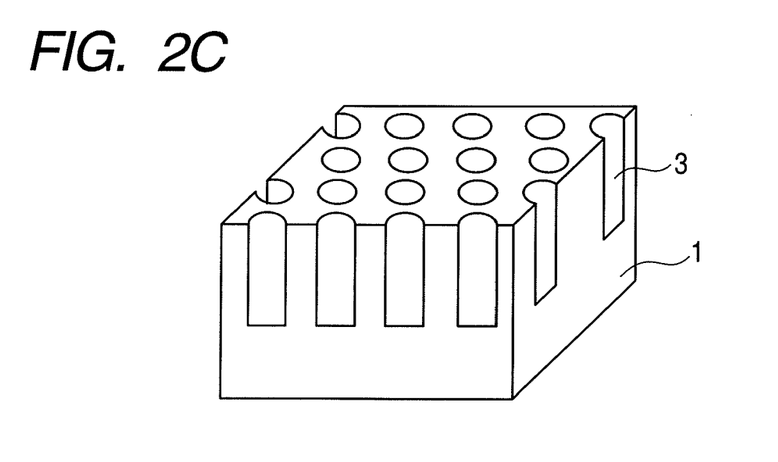

The pore 3 may penetrate the substrate 1 in the thickness direction of the substrate as illustrated in FIG. 2A, or may not penetrate the substrate 1 as illustrated in FIGS. 2B and 2C. In the case of a structure in which the pore does not penetrate the substrate 1, one may be employed in which, as illustrated in FIG. 2C, the substrate is composed of one layer (an integral-type substrate formed of one identical material) and the pore does not penetrate the layer, or in which, as illustrated in FIG. 2B, the substrate is composed of a plurality of layers wherein one layer 1a of the plurality of layers has a through-pore and the other layer 1b is free from pore. In the case of a structure in which the pore penetrates the substrate as illustrated in FIG. 2A, the so-called flow-through element can be made, which is used by transmitting a sample liquid from one surface of two facing surfaces of the detecting element to the other surface (from the front surface to the rear face). Moreover, in the case of FIG. 2B, for the layer having no pore among the plurality of layers of the substrate, materials can be selected from a wide range, and thus the strength of the detecting element can be further increased. When the transmitted light of the detecting element is used as emitted light from the detecting element, it is preferable for the layer having no pore among the plurality of layers to be transparent to the wavelengths of entering measurement light (incident light) and light subjected to detection (detection light). Here, "transparent to a specific wavelength λ" means that the transmittance of the specific wavelength A is 0.7 or higher. Light which is transmitted through the metal structure and then reflected from the layer having no pore of the substrate can be used for detection as reflected light from the detecting element. In this case, the layer is structured in such a manner that a surface (portion) reflecting wavelengths of the incident light and detection light is provided on a surface in contact with the layer having the pore.

Figure 3A:
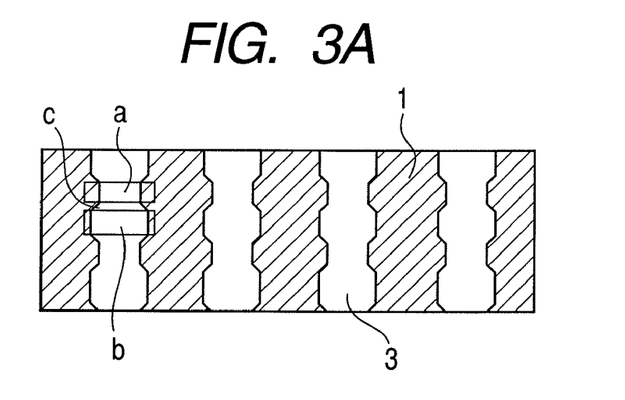
FIGS. 3A, 3B and 3C are schematic views each illustrating an example of a cross section of a substrate having pores whose pore diameters in the cross sections are different from each other in the penetrating direction according to the present invention.
Figure 3B:
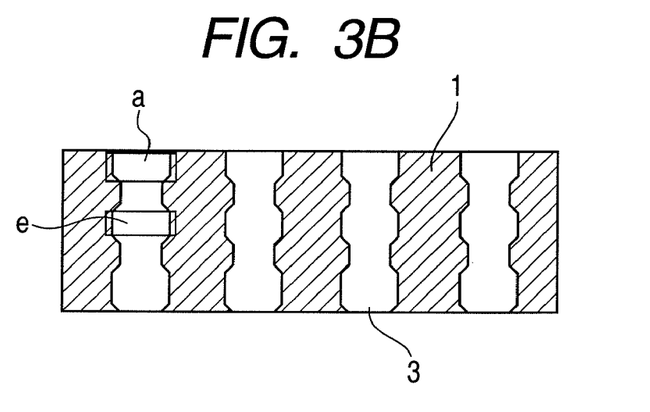

Further, it is preferable that the pore 3 is composed of a plurality of columnar parts in which the depth direction of the pore corresponds to the height direction and a part for connecting the columnar parts. More specifically, as illustrated in FIG. 3A, the pore 3 is composed of: a columnar part (pore part) a and a columnar part (pore part) b in which the depth direction of the pore corresponds to the height direction; and a connection part (pore part) c which connects the columnar part (pore part) a and the columnar part (pore part) b. As illustrated in FIG. 3A, the columnar part a and the columnar part b are preferably different from each other in the radiuses of circles in the cross sections (i.e., the pore diameters in the cross sections) where the outline of the substrate forming each of the plurality of columnar parts is cut along a face perpendicular to the height direction of the columnar part. However, as illustrated in FIG. 3B, the radiuses in the aforementioned cross sections of the outline of the substrate forming the columnar part a and the outline of the substrate forming the columnar part e may be the same. In this regard, "the substrate having columnar parts which are different from each other in the radiuses of circles in the cross sections where the outline of the substrate forming each of the columnar parts is cut along a face perpendicular to the height direction of spaces having the columnar parts" means "the substrate in which the pore diameter of a pore which appears on the cross section where the substrate is cut along the first plane perpendicular to the thickness direction of the substrate, and the pore diameter of a pore which appears on the cross section where the substrate is cut along the second plane perpendicular to the thickness direction of the substrate, are different from each other".

Figure 4A:
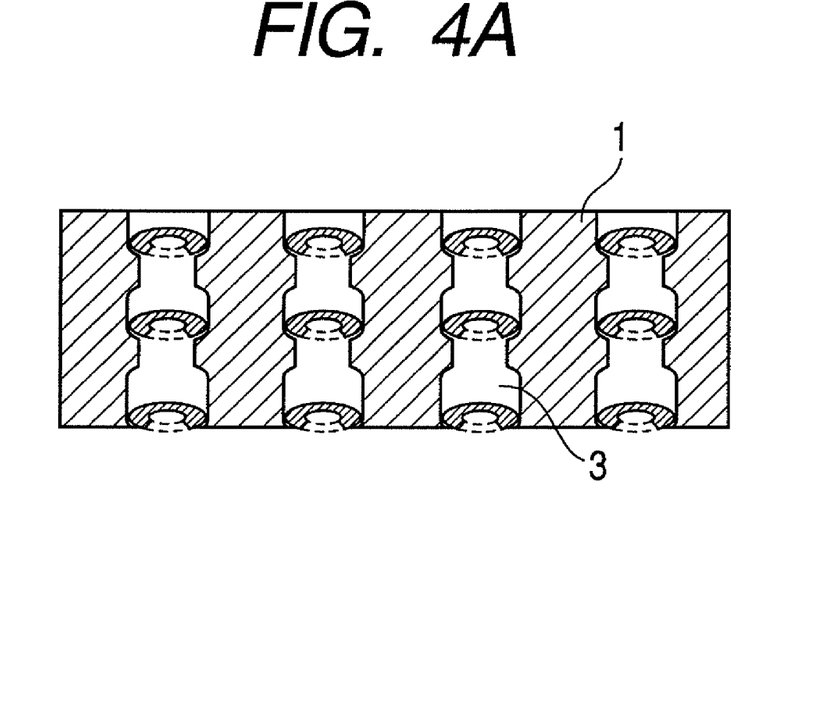
FIGS. 4A and 4B are schematic views each illustrating an example of a cross section of a detecting element having pores whose pore diameters in the cross sections are different from each other in the penetrating direction according to the present invention.
Figure 4B:
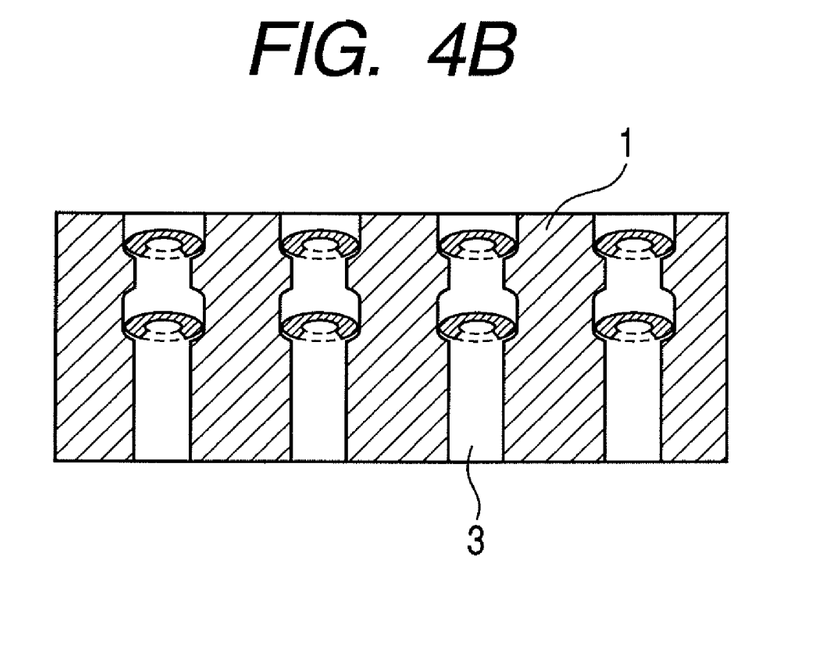

Thus, the pore is composed of a plurality of parts having columnar shapes in which the depth direction of the pore corresponds to the height direction and a part(s) for connecting the parts having the columnar shapes, to thereby facilitate the formation of the ring-shaped metal structure. Hereinafter, in some case, such a substrate is referred to as a substrate in which the pore diameters in the cross sections perpendicular to the depth direction of the pore are different from each other in the depth direction of the pore. Although detailed descriptions will be given in the following description for a production method, the pore is subjected to oblique film deposition using the substrate having such a shape, whereby a plurality of ring-shaped metal structures can be formed at once in one pore (FIGS. 4A and 4B).

Figure 3C:
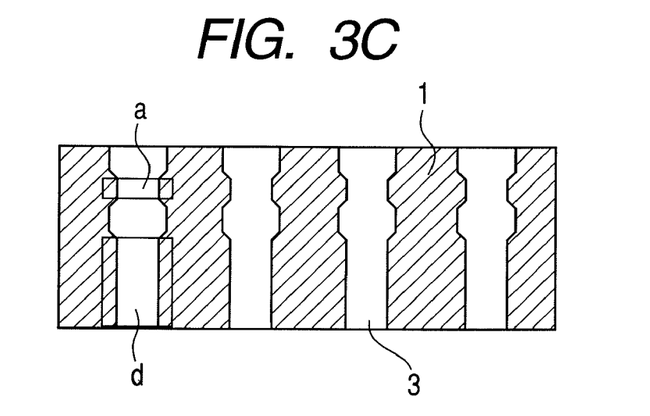

In the case of the structure illustrated in FIG. 3A, it is preferable that the radius A (pore diameter A) in the cross section of the outline of the substrate forming the columnar part a (smaller column) is 5 nm to 10 µm, and that the radius B (pore diameter B) in the cross section of the outline of the substrate forming the pore part b (larger column) having a ring shape is larger than the pore diameter A and 10 nm to 10 µm. In order to increase the number of the metal structures held per unit area of the substrate, it is preferable that as illustrated in FIG. 3A, a plurality of the columnar parts different in the pore diameters in the cross sections exist in one pore. In addition, as illustrated in FIG. 3C, the pore may further have a columnar part d whose pore diameter is the same as the diameter of the columnar part a and whose height is different from the height of the columnar part a.

In FIG. 3A, the columnar part a is referred to also as a narrow part and the columnar part b is referred to also as a bulge part.

(Metal Structure)

The metal structure of the present invention has a ring shape and is so placed as to surround the axis in the depth direction of the micropore as illustrated in FIG. 1. The metal structure having such a ring-shaped circular structure has the following features. First, as compared with a structure which has the same external shape and has no hollow portion in the center, an outer edge portion (edge part) as an area for exciting surface plasmons in the metal structure is lengthened. In the ring shape, the outer edge length is the sum of the outer periphery and the inner periphery of the ring shape. Since the outer edge and the inner edge of the ring shape in which the exciting rate of surface plasmons is high come close to each other, surface plasmons interact with each other, thereby further exciting surface plasmons. Moreover, because the ring shape has little area in which the detection ability is low as in the center portion of a structure not having such a circular structure, the proportion of an effective detection area increases. In the present invention, the detecting element is provide with the ring-shaped metal structure to utilize the above-mentioned features of the ring-shaped metal structure, so that sensitivity sufficient for the detecting element can be achieved.

The material of the metal structure 2 has only to contain a metal capable of causing a plasmon resonance phenomenon, and as such a metal, gold, silver, and copper are preferable. In particular, silver is preferably used due to high sensitivity despite of its low corrosion resistance. Moreover, gold is preferable because gold has advantages in that a stable detecting element having high corrosion resistance can be produced, and surface modification using thiol, etc. is easy. The number of the metal structures in one pore is preferably two or more. The use of the above-mentioned pore makes it possible to perform hierarchy placement of the metal structures in the thickness direction (longitudinal direction in the drawings) in the pore of the substrate, and the number of the metal structures per unit area of a contact surface (surface forming the end portion of the pore) with a sample of the substrate is increased, so that the sensitivity of the device can be increased.

It is preferable that the radius of a circle forming the outer edge of a ring-shaped metal structure is 10 nm to 10 µm. It is preferable that the radius of a circle forming the inner edge of a ring-shaped metal structure is 1 nm to 10 µm. Further, it is preferable that the band width of the metal structure is 1 nm to 1 µm. The band width is obtained by subtracting the radius of the inner edge of the metal structure in the cross section from the radius of the outer edge of the metal structure in the cross section.

(Capturing Component and Measurement Target)

On the surface of the metal structure 2, a capturing component may be disposed. When the metal structure itself has a function of capturing a target substance, the capturing component may not be disposed, whereas, when the metal structure itself does not have a function of capturing a target substance, the capturing component for capturing a target substance in a sample may be disposed on the surface of the metal structure.

A capturing component to be used is a substance involved in the selection of a target substance contained in a sample liquid. For example, a substance (so-called receptor) which directly reacts selectively with a target substance in a sample may be used. Alternatively, a substance may be used which can indirectly determine a target substances such as a substance which is involved in a reaction of a target substance (e.g., a substance which selectively gives a catalytic action to a reaction of a target substance) and a substance which inactivates a substance other than a target substance in a sample. In addition, the capturing component may also have a function of displaying the presence or absence or the degree of detection, e.g., a function of reacting with a substance discharged from a receptor or a residual substance to show color development.

The target substance is not limited to a biological substance and is not limited concerning the size. However, it is preferable that the target substance is: a biological substance contained in an organism, such as saccharides protein, amino acid, an antibody, an antigen and a pseudo-antigen, vitamin, and a gene; substances related thereto; and a pseudo biological substance which is artificially synthesized.

Therefore, as the capturing component, an enzyme, a sugar chain, a catalyst, an antibody, an antigen, a gene, a color reagent, etc., can be used, but the capturing component is not limited thereto.

Next, immobilization or support of the capturing component to the surface of the metal structure will be described. The above-mentioned capturing component is immobilized to or supported on the surface of the metal structure by a bonding method using, for example, a covalent bond and an ionic bond, an adsorption method, etc. However, there is no limitation on the immobilization method or supporting method insofar as the capturing component can be effectively immobilized or supported in such a state that the capturing components can be used for detection.

In the case of the bonding method, a capturing component having a reaction group which can directly act on the surface of the metal structure may be reacted and bonded to the surface of the metal structure. Alternatively, a crosslinking material which can directly act on the surface of the metal structure may be reacted and bonded to the surface of the metal structure, and then a capturing component may be reacted and bonded to the crosslinking material. For example, when the metal structure contains gold, silver, or copper, a capturing component having a thiol group, an amino group, etc., can be directly immobilized. In addition, A silane coupling agent having a thiol group, amino group, etc. is reacted to the surface of the metal structure, and then a capturing component is bonded to the silane coupling agent, whereby the capturing component can be supported on the metal structure.

In the case of the adsorption method, among possible combinations of a capturing component and a material of the metal structure, a combination having suitable affinity may be selected. Further, the surface of the metal structure may be subjected to surface modification to form a surface having suitable affinity, and then a capturing component may be immobilized.

Next, an example of a method of producing the detecting element of the present invention will be described.

The method of producing the detecting element of the present invention includes:

(A) preparing a substrate having a pore in which the thickness direction of the substrate corresponds to the depth direction of the pore and in which part of the substrate forming the pore constitutes part of the outer surface of the substrate; and (B) producing a ring-shaped metal structure in the pore by projecting a material for forming the metal structure in a direction crossing the depth direction of the pore.

Hereinafter, each step will be described.

Step (A)

(Step of Preparing a Substrate Having a Pore)

In this step, the above-mentioned substrate having a pore is prepared. The substrate is not limited concerning the material, dimension, and shape. The pore has only to serve as a foothold for forming a ring-shaped metal structure as described above. For example, an arbitrary substrate or film can be used, in which a pore is formed by processing treatment such as etching. In addition, an anodized alumina formed on the surface of aluminum by anodizing aluminum in an acidic electrolyte has columnar through-pores on the surface, and thus is preferably used. The anodized alumina is suitable for controlling the shape and size of the metal structure, because the pore diameter and pore depth can be relatively freely controlled. Moreover, a polycarbonate membrane filter also has through-pores, and is commercially available. Thus, the polycarbonate membrane filter can be used conveniently.

When a ring-shape metal structure which is uniform in the circumferential direction is formed, as illustrated in FIGS. 2A to 2C, it is preferable to use a substrate having a pore linearly extending in the thickness direction of the substrate which is a direction substantially orthogonal to a face forming the end portion of the pore among the faces of the substrate.

Moreover, when a substrate is composed of a plurality of layers and through-pores are formed in a specific layer, another layer is adhered to the layer in which the through-pores have been formed, to thereby obtain a substrate.

As a method of forming a substrate in which the pore diameters in cross sections perpendicular to the depth direction of a pore are different from each other in the depth direction of the pore, one is cited which involves superimposing one on another aluminum alloy films different from each other in compositions or composition ratios, and performing pore wide treatment by anodization and etching. When an aluminum alloy is anodized, as in the anodized alumina, a pore is formed on the surface. When the anodized alumina alloy is further subjected to pore wide treatment, the enlargement degree of the pore diameter varies depending on the type and content ratio of an additional element contained in the aluminum alloy. By utilizing the differences, a substrate can be prepared in which the pore diameters of cross sections perpendicular to the depth direction of the pore are different from each other in the depth direction of the pore as illustrated in FIGS. 3A and 3C. However, the method is not limited to the above-mentioned method, and any methods can be used in the present invention insofar as they can provide a substrate having a pore whose shape is suitable for the present invention.

Step (B)

(Step of Producing a Ring-Shaped Metal Structure in a Pore)

Figure 5A:
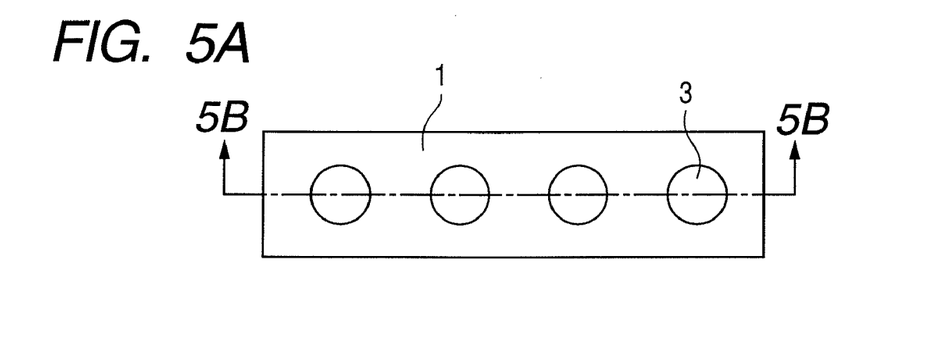
Figure 5B:
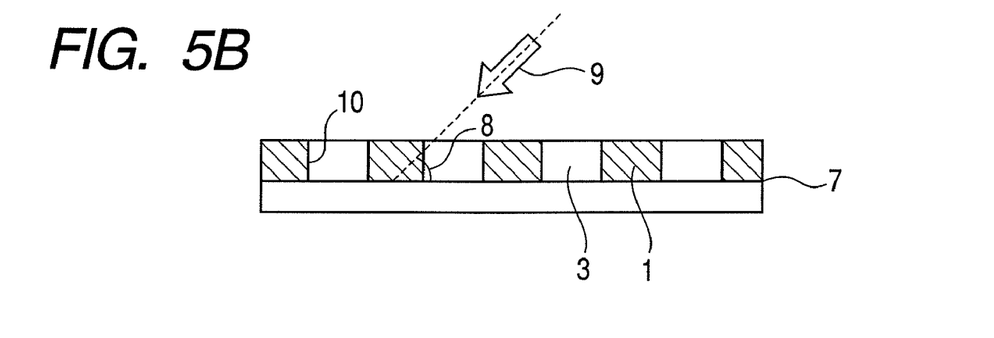
FIG. 5B is a cross-sectional view taken along the line 5B-5B of FIG. 5A.

In this step, a metal structure is produced in a pore by an oblique film deposition method which involves projecting a material for forming a metal structure from an oblique direction with respect to the opening direction of the pore (in other words, in the depth direction of the pore). In the present invention, the "oblique film deposition method" means depositing materials in the pore from an oblique direction, i.e., a direction in which a material is projected (or deposited) crosses an opening direction 7 of the pore (a direction parallel to a contact surface 4 which is a surface forming the end portion of the pore). To be specific, as illustrated in FIG. 5B, a material for forming the metal structure is projected into an outline (wall surface) 10, which forms the pore of a substrate, from a projection direction 9 at a projection angle 8 to an opening direction 7 of the pore. Thereby, it is possible to form a plurality of ring-shaped metal structures at once in the pore. FIG. 5A is a projection view when a substrate is irradiated with light from the outside of the substrate in a direction parallel to the thickness direction of the substrate. FIG. 5B is a cross-sectional view taken along the line 5B-5B of FIG. 5A.

Figure 5C:
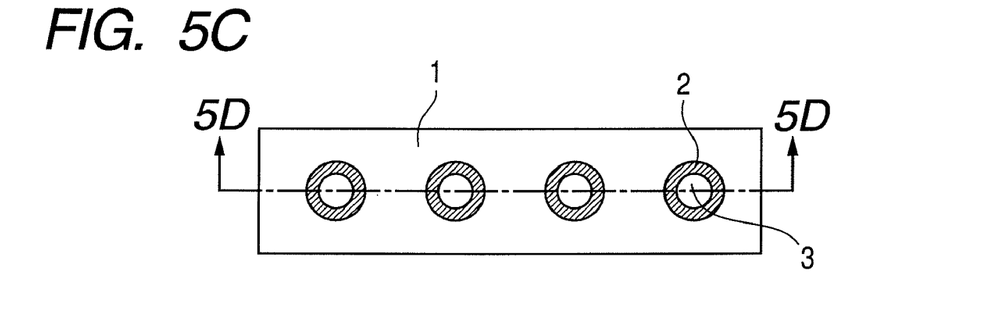
Figure 5D:
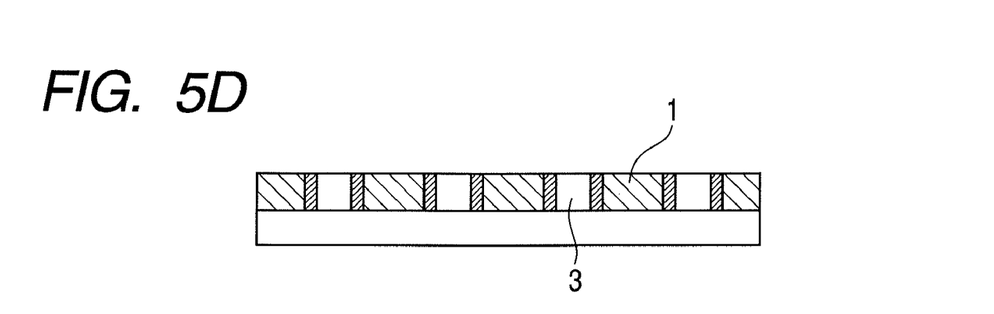
FIG. 5D is a cross-sectional view taken along the line 5D-5D of FIG. 5C.
Figure 6A:
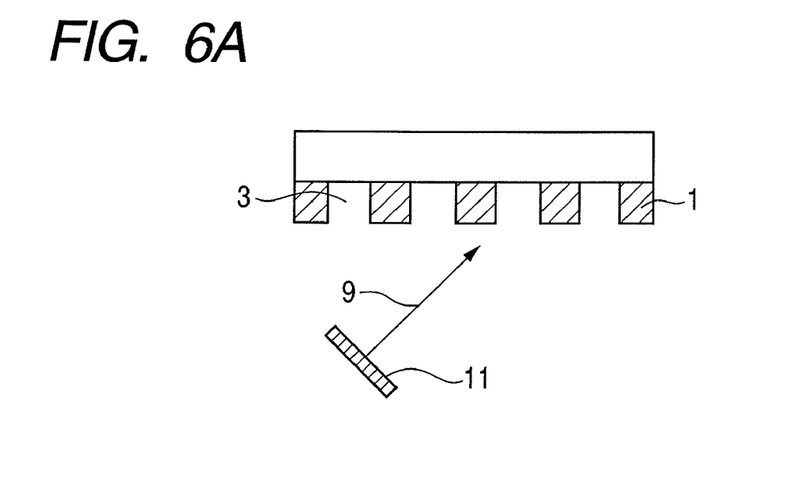
FIGS. 6A, 6B and 6C are schematic views each illustrating a projection of a material by an oblique film deposition method.
Figure 6B:
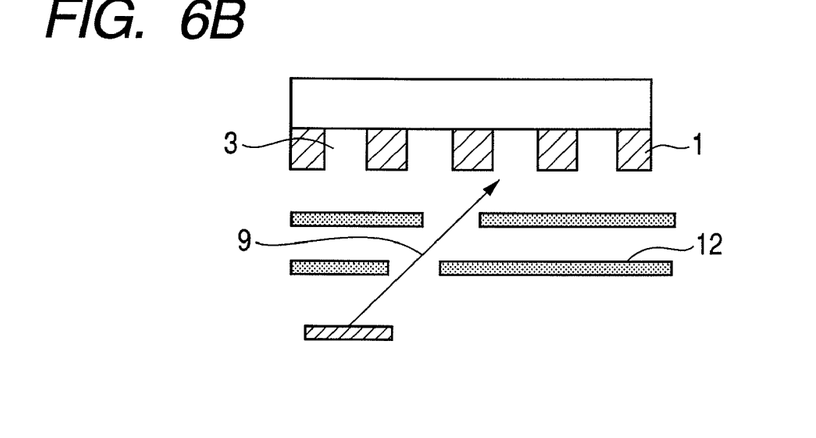
Figure 6C:
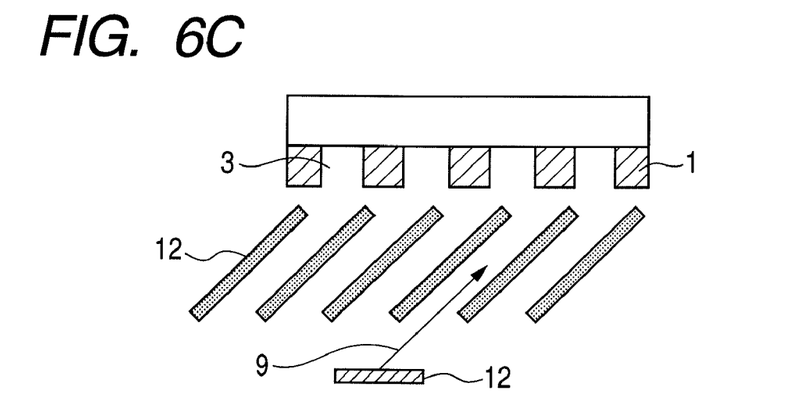

As the film deposition method, an RF sputtering method, an ion beam sputtering method, a vacuum deposition method, a CVD method, etc., can be used. In the present invention, by utilizing the oblique film deposition method, a formation material can be deposited primarily on the inner wall surface of the pore. Further, during the deposition process, a substrate is so rotated as to form a ring-shaped metal structure in the pore as illustrated in FIGS. 5C and 5D. FIG. 5C is a projection view when the substrate and the metal structure are externally irradiated with light in a direction parallel to the thickness direction of the substrate. FIG. 5D is a cross-sectional view taken along the line 5D-5D of FIG. 5C. When using, for example, a sputtering method as the film deposition method, as illustrated in FIG. 6, a target is placed in such a positional relationship that a predetermined angle is formed between the traveling direction of sputtering particles (a projection direction 9 of a material) which are flown from a target 11 and projected and the opening direction of the pore have. Then, as illustrated in FIG. 6A, the sputtering particles are deposited in the pore while maintaining the state (oblique sputtering). The projection direction of the material may be controlled using a slit 12 having a predetermined opening as illustrated in FIGS. 6B and 6C. When such a slit 12 is used, the controllability of the projection direction is improved, and, in addition thereto, only the sputtering particles which pass through the opening can be deposited to the substrate, whereby the controllability of a deposition area can be improved.

By performing the steps (A) and (B), a detecting element can be produced.

Next, the detecting device in the present invention will be described.

(Detecting Device)

The detecting device in the present invention includes a holding mechanism for holding the above-mentioned detecting element, a light source for irradiating the detecting element with light, and a light receiving element for detecting light emitted from the detecting element.

When a sample liquid containing a target substance is brought into contact with the detecting element, the target substance contained in the sample liquid is captured by a capturing component which exists in a metal structure or on the surface of the metal structure, whereby optical properties in the vicinity of the metal structure change. The changes of the optical properties in the vicinity of the metal structure can be detected by irradiating the detecting element with light and detecting the characteristics of the emitted light from the detecting element (e.g., transmitted light or reflected light) with the light receiving element. The detecting device can be provided with a reaction chamber in which the sample liquid and the detecting element are brought into contact with each other.

EXAMPLES

Hereinafter, the present invention will be described in more detail with reference to examples, and is not limited thereto. In the present invention, materials, composition conditions, reaction conditions, and film formation conditions, etc., can be changed freely insofar as a detecting element and a detecting device having the same functions can be obtained.

Example 1

This example describes an example of producing a detecting element by forming a quartz substrate in which pores are formed by a photolithography method into a substrate integrated with a support, and forming a ring-shaped metal structure formed of gold in the pore by an oblique sputtering method. This example describes an example in which the substrate is integrated with the support, which is easily and simply produced and is excellent in strength.

First, a quartz substrate is prepared, and then a plurality of columnar pores are formed in the surface of the substrate using a photolithography method as illustrated in FIG. 2C, to thereby obtain a substrate. In the pores, the inner diameter is about 250 nm, the depth is about 400 nm, and the interval between the pores is about 500 nm. During the process, photoresist layers formed in areas other than the pores may be removed, but may be left on the surface of the substrate in order to remove metal deposited to extra areas other than the pores in a process, as described later, of forming a metal structure. Next, gold is deposited to the substrate by an oblique sputtering method. The projection degree is 45° with respect to the substrate surface (plane) on which the pores open. More specifically, the projection degree is 45° with respect to the central axis of the pore. According to this treatment, a ring-shaped metal structure formed of gold is formed in the pore. By suitably controlling the projection angle, the shapes such as the thickness and band width of a ring-shaped structure to be formed can be controlled. In order to improve the adhesiveness between gold and quartz, titanium, chromium, etc., may be deposited as a foundation layer by an oblique sputtering method before depositing gold. Further, gold deposited in areas on the surface of the substrate other than the pores may be removed, where a removing method, such as polishing, may be used. When the above-mentioned photoresist layers of the surface of the substrate is left, extra gold can be removed in a lift-off manner by removing the photoresist layer. Through the above-mentioned process, a detecting element is produced which is provided with a ring-shaped metal structure formed of gold in the pore of the quartz substrate.

Example 2

This example describes an example of producing a detecting element by preparing, as a substrate, an alumina layer in which pores are formed by anodization of aluminum, and forming a ring-shaped structure formed of gold in the pore by an oblique sputtering method. This example describes an example in which a substrate is composed of a plurality of layers and the layers are formed of materials different from each other, respectively, which is suitable for a case where the detecting element is used by removing later the substrate and for a case where the detecting element utilizes a light reflected from a support after passing through the substrate.

First, a silicon substrate is prepared as one layer (serving as a support), and then an aluminum layer is formed on the silicon substrate. During the process, in order to improve the adhesiveness between the layers, a thin film formed of titanium or chromium may be formed as an adhesion layer between two foundation layers. Next, the aluminum layer on the silicon substrate is washed, and then the washed aluminum layer is anodized at 40 V in a 0.3 M oxalic acid solution. Thus, columnar pores in the layer thickness direction are formed while the surface of aluminum being oxidized into alumina, to thereby obtain a substrate. By suitably controlling the anodic-oxidation voltage, the interval between the pores can be controlled, and by suitably controlling an anodic-oxidation time, the pore depth can be controlled. Thus, the anodic-oxidation conditions may be suitably selected. Further, the pore diameter is enlarged by immersing the substrate in a 5 wt % phosphoric acid for a given time (pore wide treatment), whereby a substrate having pores with desired sizes can be obtained. The pore diameter can be controlled by suitably controlling temperature, immersion time, a type of acid, concentration, etc., and thus the pore wide conditions may be suitably selected. Through the above-mentioned process, a substrate having pores is produced. Next, as in Example 1, gold is deposited on this substrate by oblique sputtering method.

Through the above-mentioned process, a detecting element is produced which is provided with a ring-shaped metal structure formed of gold in the pore of the alumina layer formed on the silicon layer.

Example 3

This example describes an example of producing a detecting element by preparing a substrate in which the pore diameters in the cross sections of the pore are different from each other in the penetrating direction by using a film formed by superimposing aluminum alloy layers, whose compositions are different from each other, and forming a plurality of ring-shaped gold structures in the pore by an oblique sputtering method. As in this example, by forming a plurality of metal structures in the pore, the number of the metal structures per unit area can be increased, which contributes to the improvement of the sensitivity.

Figure 7A:
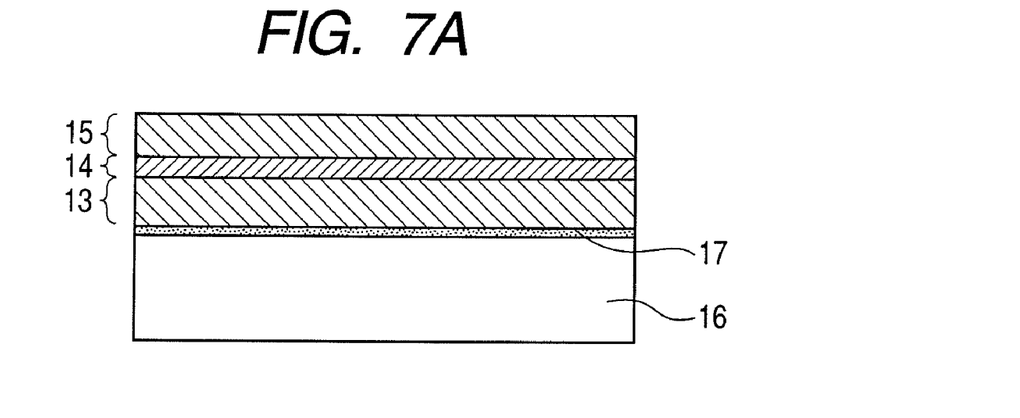
FIGS. 7A, 7B and 7C are schematic views each illustrating a production process of a detecting element in Example 3.
Figure 7B:
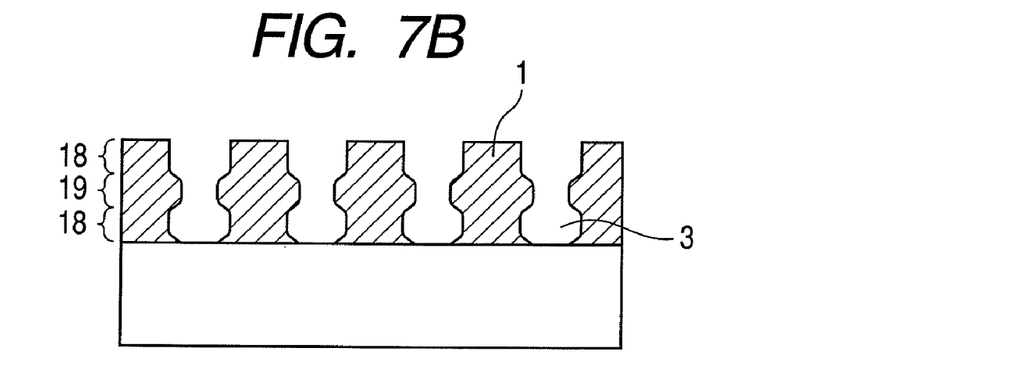

First, a silicon substrate is prepared to be used as a silicon layer 16, and an aluminum tungsten alloy layer 13 is formed on the silicon layer 16 as illustrated in FIG. 7A. In this case, a thin film formed of titanium (titanium layer) 17 may be formed as an adhesion layer between the silicon layer 16 and the aluminum tungsten alloy layer 13. An aluminum hafnium alloy layer 14 is formed on the aluminum tungsten alloy layer 13. Further, on the aluminum hafnium alloy layer 14, an aluminum tungsten alloy is formed again to be used as an aluminum tungsten alloy layer 15. Subsequently, the substrate is anodized by applying a voltage of 80 V in a 0.3 mol/L phosphoric acid aqueous solution having a bath temperature of 100° C. By suitably controlling the anodic-oxidation voltage, the interval between the pores can be controlled, and by suitably controlling an anodic-oxidation time, the pore depth can be controlled. Thus, the anodic-oxidation conditions may be suitably selected. After the anodization, by immersing a sample in a 0.3 M phosphoric acid aqueous solution having a bath temperature of 22.5° C. to subject the sample to pore wide treatment, a substrate having a bulge part 18 and a narrow part 19 as illustrated in FIG. 7B can be obtained. The pore diameter can be adjusted by suitably controlling temperature, immersion time, a type of acid, concentration, etc., and thus the pore wide conditions may be suitably selected.

Through the above-mentioned process, a substrate can be produced in which, in other words, the pore diameters in cross sections perpendicular to the depth direction of the pore are different from each other in the depth direction of the pore.

Figure 7C:
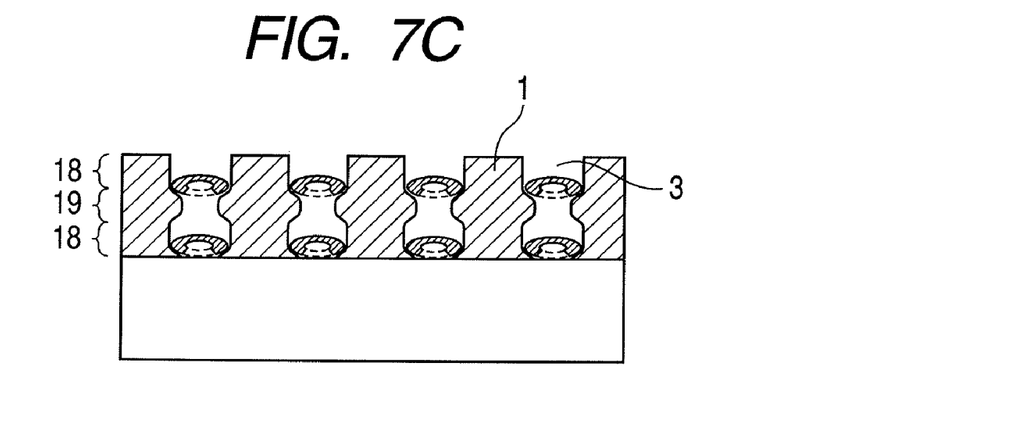

Next, gold is deposited to the substrate by an oblique sputtering method as in Example 1. When the projection angle is suitably selected in accordance with the pore diameter and the pore depth, a plurality of ring-shaped metal structures are almost each independently formed in the pore as schematically illustrated in FIG. 7C.

Through the above-mentioned process, a detecting element is produced which is provided with a plurality of ring-shaped metal structures formed of gold in the pore in which the pore diameters of cross sections perpendicular to the depth direction of the pore are different from each other in the depth direction of the pore.

Example 4

This example describes an example of providing a detecting element by forming a ring-shaped structural member formed of gold in the pore by an oblique sputtering method, using a polycarbonate membrane filter having vertical pores as a substrate. As in this example, the substrate having through-pores can be used as it is for flow-through detection.

First, a substrate having vertical pores is prepared. Such a substrate is commercially available, and can be preferably used in the present invention. For example, Nuclepore membranes (produced by Nomura Micro Science Co., Ltd.) have various pore diameters, and can be preferably used. Next, gold is deposited on the substrate by an oblique sputtering method as in Example 1. By suitably selecting the projection angle in accordance with the pore diameter and the pore depth, a ring-shaped metal structure can be formed in the pore as illustrated in FIG. 1A.

Through the above-mentioned process, a detecting element equipped with the ring-shaped metal structure formed of gold in the pore of the substrate can be produced.

Example 5

This example describes an example in which a capturing component is supported on the detective element produced in Example 1, and further, a target substance was detected using the detecting device. Note that this example describes an example of detecting a target substance by measuring the characteristics of light transmitted through the detecting element.

In the beginning, an operation of immobilizing an antibody as a capturing component to the surface of a ring-shaped metal structure formed of gold will be described. In this example, a rabbit anti-mouse IgG antibody is used as an antibody. First, 11-mercaptoundecanoic acid having a thiol group in an ethanol solution is applied to a pore-opened surface (surface forming the end portion of the pore) of the quartz substrate of the detecting element produced in Example 1. A carboxyl group is exposed to the surface of the ring-shaped metal structure by the operation. Next, an N-hydroxysulfosuccinimide aqueous solution and a 1-ethyl-3-[3-dimethylamino]propyl carbodiimide hydrochloride aqueous solution are likewise applied. A succinimide group is exposed to the surface of the ring-shaped metal structure by the operations. Subsequently, a substrate is immersed in a rabbit anti-mouse IgG antibody/tris-hydrochloric acid buffer solution (pH 8.0). Then, the succinimide group formed on the surface of the ring-shaped metal structure is reacted with the amino group of the rabbit anti-mouse IgG antibody, to thereby immobilize the rabbit anti-mouse IgG antibody on the surface of the metal structure. Through the above-mentioned operations, a detecting element having the rabbit anti-mouse IgG antibody as a capturing component can be produced.

Next, an example of a detecting device will be described. This example describes an example of detection by light transmitted through the detecting element.

Figure 8A:
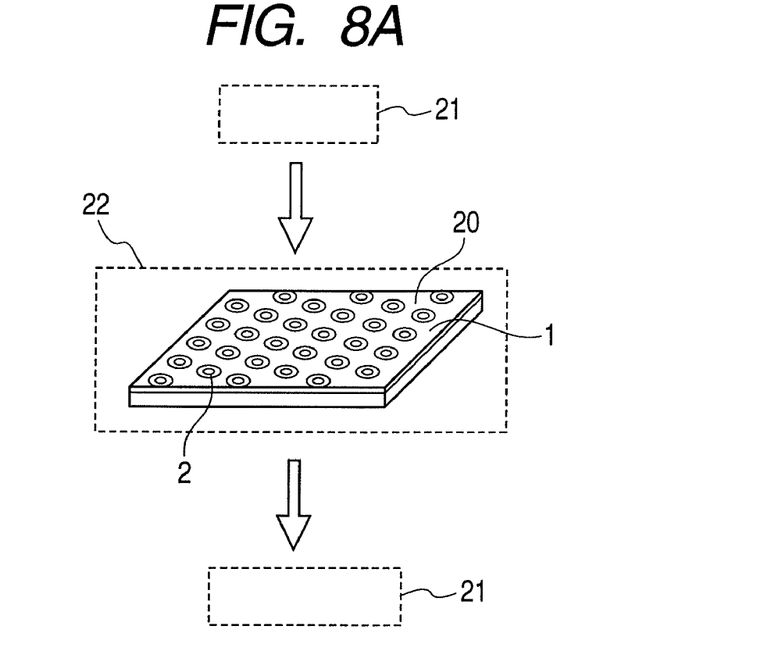
FIGS. 8A and 8B are schematic views each illustrating an example of detecting devices in Examples 5, 6, and 7

FIG. 8A is a view schematically illustrating a detecting device of this example. The detecting device includes a detecting element-holding mechanism, a light source, and a light receiving element. As schematically illustrated in FIG. 8A, the light source at the time of detection is positioned so that a detecting element can be irradiated with measurement light, and the light receiving element is positioned so that the characteristics of the measurement light transmitted through the detecting element can be detected. In addition to the above, the light receiving element may include a spectrum detector (not shown). Further, it is preferable to provide an arithmetic device which calculates changes in the detected characteristics and a display unit for displaying the detection results, etc., which are not illustrated in the drawings.

Next, an example of detecting a target substance will be described.

First, a detecting element-holding mechanism 22, a detecting element 20, a light source 21, and a light receiving element 23 are placed in the above-mentioned positional relationship at the time of detection, to thereby detect a spectrum. After that, a sample solution containing a phosphoric acid buffer solution containing mouse IgG as a target substance is applied to the detecting element 20, to thereby bring the sample solution into contact with the detecting element 20 to react with a capturing component. After the reaction, the surface of the metal structure 2 may be washed with a phosphoric acid buffer solution. Then, the detecting element 20, the light source 21, and the light receiving element 23 are placed again in the same positional relationship as at the time of detection, to thereby detect a spectrum. Spectral changes before and after applying the sample solution are derived from changes in the plasmon resonance conditions of the metal structure 2. The changes means that an antigen-antibody reaction occurs on the detecting element and the target substance has been captured by the capturing component. Thus, the target substance in the sample can be detected by detecting the spectral changes.

As for the relationship between the spectral changes and the concentrations of the target substance, when the relationship between the spectral changes and the concentrations is obtained beforehand using standard samples having various known concentrations, and a calibration curve is prepared on the basis of the relationship to thereby obtain a function between the spectral changes and the concentrations, the concentration of the target substance can be found from the spectral changes using this function at the time of actual measurement.

Here, the term "spectral changes" is used. The spectral changes may be changes in spectral peak at a wavelength having the maximum value, or may be changes in the peak shape, such as a half-value width of a spectral peak waveform. Further, light intensities at one or two or more wavelength points may be used.

As described above, according to the present invention, the target substance in the sample can be detected with sufficient sensitivity.

Example 6

This example is an example in which a capturing component is supported on the detective element produced in Example 2, and further, a target substance was detected using the detecting device. In this example, a target substance is detected by measuring the characteristics of light reflected from the detecting element.

First, an antibody is immobilized as a capturing component on the surface of a ring-shaped gold structure in the same manner as in Example 5. Also in this example, a rabbit anti-mouse IgG antibody is used as an antibody. Through the process, a detecting element having a rabbit anti-mouse IgG antibody as a capturing component can be produced.

Next, an example of a detecting device will be described. Here, an example is described in which detection is carried out using light reflected from the detecting element.

Figure 8B:
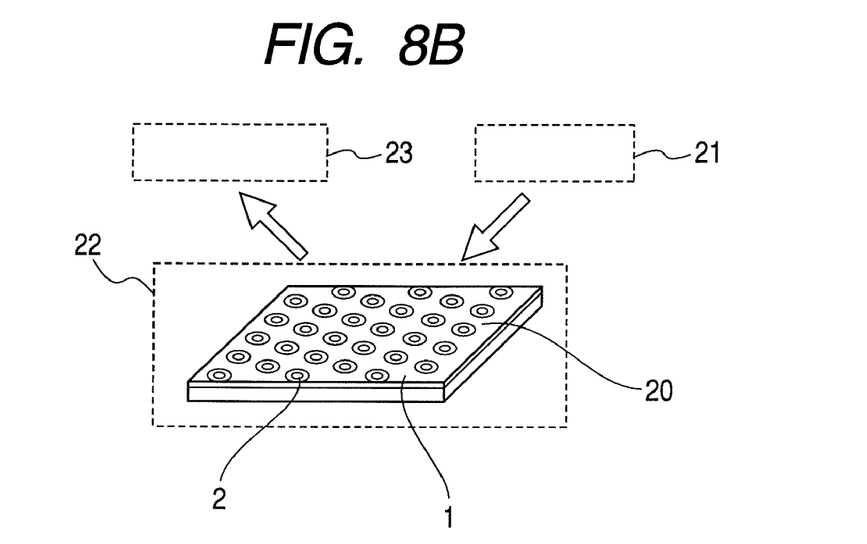

FIG. 8B is a view schematically illustrating a detecting device of this example. The detecting device includes a detecting element-holding mechanism 22, a light source 21, a detecting element 20, and a light receiving element 23. As schematically illustrated in FIG. 8B, the light source 21 at the time of detection is positioned so that a detecting element 20 can be irradiated with a measurement light and the light receiving element 23 is positioned so that the characteristics of the measurement light reflected from the detecting element 20 can be detected. In addition to the above, the light receiving element 23 may be provided with a spectrum detector (not shown). Further, it is preferable to provide an arithmetic device which calculates changes in the detected characteristics and a display unit for displaying the detection results, etc., which are not illustrated in the drawings.

Next, an example of detecting a target substance will be described.

First, a detecting element 20, a light source 21, and a light receiving element 23 are placed in the above-mentioned positional relationship at the time of detection, to thereby detect a spectrum. After that, a sample solution containing a phosphoric acid buffer solution containing mouse IgG as a target substance is applied to the detecting element 20, to thereby bring the sample solution into contact with the detecting element 20 to react with a capturing component. After the reaction, the surface of the metal structure 2 may be washed with a phosphoric acid buffer solution. Then, the detecting element 20, the light source 21, and the light receiving element 23 are arranged again in the same positional relationship as at the time of detection, to thereby detect a spectrum. The spectral changes before and after applying the sample solution are derived from changes in the plasmon resonance conditions of the metal structure 2. The changes means that an antigen-antibody reaction occurs on the detecting element and the target substance has been captured by the capturing component. Thus, the target substance in the sample can be detected by detecting the spectral changes.

The concentration of the target substance can also be obtained by preparing a calibration curve as in Example 5. Moreover, as in Example 5, the spectral changes may be changes in spectral peak wavelength, or may be changes in the spectral peak shape. Further, light intensities at one or more wavelength points may be used.

As described above, according to the present invention, the target substance in the sample can be detected with sufficient sensitivity.

Example 7

This example is an example in which a capturing component is supported on the detecting element produced in Example 4, and further a target substance is detected using the detecting device. In this example, a target substance is captured by a flow-through method, and then detected.

First, an antibody is immobilized as a capturing component on the surface of a ring-shaped gold structure in the same manner as in Example 5. Also in this example, a rabbit anti-mouse IgG antibody is used as an antibody. Through the process, a detecting element having a rabbit anti-mouse IgG antibody as a capturing component can be produced.

Next, a method of capturing a target substance by a flow-through method and detecting the target substance, using the detecting element, will be described.

Figure 9A:
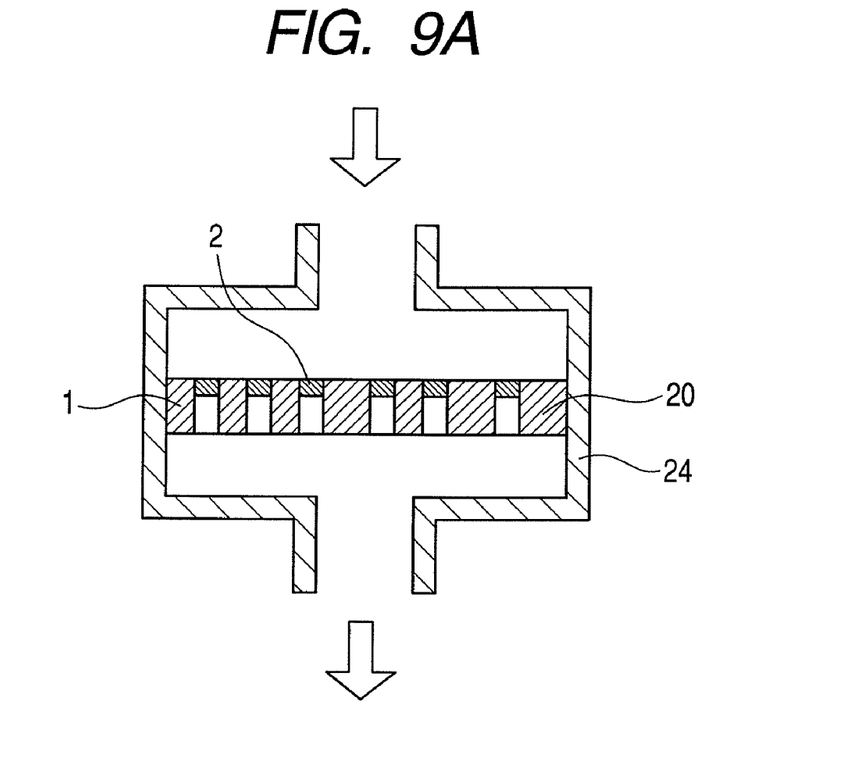
FIGS. 9A and 9B are schematic views each illustrating an example of a flow-through method in Example 7.
Figure 9B:
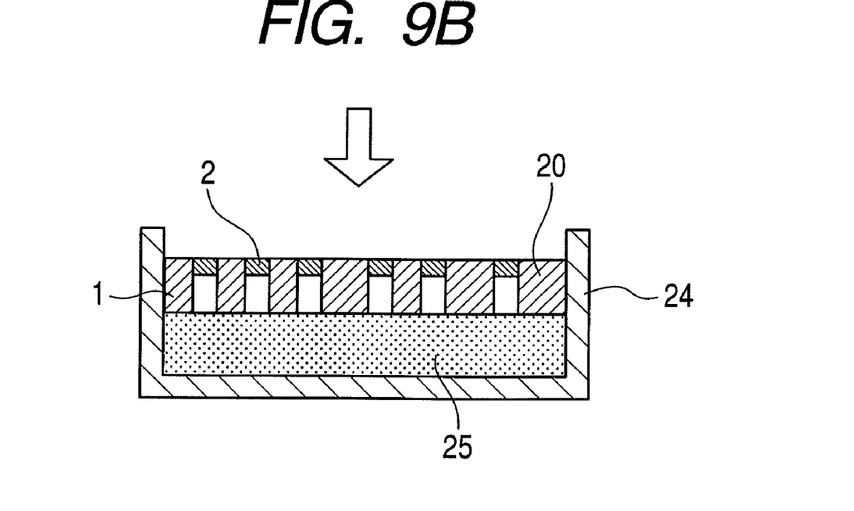

First, using the detecting device used in Example 5 or 6, a detecting element is irradiated with measurement light, and the spectrum of light which is transmitted through or reflected from the detecting element is detected. After that, a sample liquid containing a phosphoric acid buffer solution containing mouse IgG as a target substance is applied to the detecting element by the flow-through method, to thereby bring the sample solution into contact with the detecting element to react with a capturing component. Because the metal structure in the present invention has a ring shape, space exists inside the pore, which facilitates the sample solution to pass through. Application of the sample solution by the flow-through method can be performed by introducing the sample solution from one side of the detecting element, for example, the membrane in Example 4, passing the sample solution through the pore, and discharging the sample solution from the other side. The Application of the sample solution by the flow-through method may be performed using a normal method. For example, as illustrated in FIG. 9A, the detecting element 20 may be placed inside a cartridge 24, and a negative pressure or a positive pressure is applied by a pump, a syringe, etc. to pass the sample solution through the pore. Alternatively, as illustrated in FIG. 9B, an absorbent 25 may be bought into contact with one side to pass the sample liquid through the pore.

After the reaction, the surface of the metal structure may be washed with a phosphoric acid buffer solution. Thereafter, the spectrum is detected again in the same manner as at the time of detection. The spectral changes before and after applying the sample solution are derived from changes in the plasmon resonance conditions of the metal structure. The spectral changes mean that an antigen-antibody reaction occurs on the detecting element and the target substance has been captured by the capturing component. Thus, the target substance in the sample can be detected by detecting the spectral changes.

The concentration of the target substance can also be determined by preparing a calibration curve as in Example 5. In addition, as in Example 5, the spectral changes may be changes in the spectral peak wavelength, or may be changes in the spectral peak shape. Further, light intensities at one or more wavelength points may be used.

As described above, according to the present invention, the target substance in the sample can be detected with sufficient sensitivity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-145287, filed May 31, 2007, which is hereby incorporated by reference herein in its entirety.

What is claimed is:

1. A detecting element for detecting a target substance in a sample, comprising:
    a substrate having a pore, in which a thickness direction of the substrate corresponds to a depth direction of the pore; and
    a plurality of metal structures disposed in the pore, wherein the plurality of metal structures have a ring shape and are arranged linearly in the thickness direction of the substrate.

2. A detecting element according to claim 1, wherein the pore penetrates through the substrate.

3. A detecting element according to claim 1, wherein:
    the pore comprises a plurality of sections in which the depth direction of the pore corresponds to a height direction of a plurality of columnar sections and intermediate sections for connecting the plurality of columnar sections; and
    the metal structure exists in the columnar sections.

4. A detecting element according to claim 1, wherein a pore diameter of a first pore which appears in a cross section cut along a first surface perpendicular to the thickness direction of the substrate and a pore diameter of a second pore which appears in a cross section cut along a second surface perpendicular to the thickness direction of the substrate are different from each other.

5. A detecting element according to claim 1, wherein the metal structure comprises gold or silver.

6. A detecting element according to claim 1, wherein the metal structure has, on the surface thereof, a capturing component for capturing the target substance in the sample.

7. A detecting device for detecting a target substance in a sample by utilizing a Plasmon resonance method, comprising:
    the detecting element according to any one of claims 1 to 6;
    a holding mechanism for holding the detecting element;
    a light source for irradiating the detecting element with light; and
    a light receiving element for detecting light emitted from the detecting element.

8. A detecting device according to claim 7, further comprising a reaction chamber for bringing the sample into contact with the detecting element.

9. A detecting element according to claim 1, wherein a pore length of a first pore in the thickness direction of the substrate and a pore length of a second pore in the thickness direction of the substrate are different from each other.

10. A method of producing a detecting element for detecting a target substance in a sample by utilizing a plasmon resonance method, comprising the steps of:
    preparing a substrate having a pore, in which a thickness direction of the substrate corresponds to a depth direction of the pore and in which part of the substrate forming the pore forms part of an outer surface of the substrate;
    providing a plurality of ring-shaped metal structures in the pore by projecting a material for forming the metal structures in a direction crossing the depth direction of the pore; and
    linearly arranging the plurality of metal structures in the thickness direction of the substrate.

11. A method of producing a detecting element according to claim 10, wherein the pore comprises a plurality of sections in which the depth direction of the pore corresponds to a height direction of a plurality of columnar sections and intermediate sections for connecting the plurality of columnar sections.

12. A method of producing a detecting element according to claim 10, further comprising the step of providing a pore diameter of a first pore which appears in a cross section cut along a first surface perpendicular to the thickness direction of the substrate and a pore diameter of a second pore which appears in a cross section cut along a second surface perpendicular to the thickness direction of the substrate to be different from each other.

13. A method of producing a detecting element according to claim 10, further comprising the step of providing a pore length of a first pore in the thickness direction of the substrate and a pore length of a second pore along the thickness direction of the substrate to be different from each other.

* * * * *